US011894128B2

(12) United States Patent
Streich et al.

(10) Patent No.: US 11,894,128 B2
(45) Date of Patent: Feb. 6, 2024

(54) REVENUE CYCLE WORKFORCE MANAGEMENT

(71) Applicant: CERNER INNOVATION, INC., Kansas City, KS (US)

(72) Inventors: Brian Streich, Kansas City, MO (US); Kelley Bergstrom, Kansas City, KS (US); Mark Sullivan, Kansas City, KS (US); Michael D. Myers, Kansas City, KS (US)

(73) Assignee: CERNER INNOVATION, INC., Kansas City, MO (US)

( * ) Notice: Subject to any disclaimer, the term of this patent is extended or adjusted under 35 U.S.C. 154(b) by 469 days.

(21) Appl. No.: 16/731,422

(22) Filed: Dec. 31, 2019

(65) Prior Publication Data

US 2021/0202075 A1    Jul. 1, 2021

(51) Int. Cl.
*G06Q 10/00* (2023.01)
*G16H 40/20* (2018.01)
(Continued)

(52) U.S. Cl.
CPC .............. *G16H 40/20* (2018.01); *G06N 5/04* (2013.01); *G06Q 10/0637* (2013.01);
(Continued)

(58) Field of Classification Search
None
See application file for complete search history.

(56) References Cited

U.S. PATENT DOCUMENTS

| 8,688,480 B1 * | 4/2014 | Singh | G06Q 10/10 |
| | | | 705/2 |
| 2003/0097317 A1 * | 5/2003 | Burk | G06Q 10/06 |
| | | | 705/30 |

(Continued)

FOREIGN PATENT DOCUMENTS

| WO | WO-2015123466 A1 * | 8/2015 | ........... G06F 19/327 |
| WO | WO-2018141012 A1 * | 8/2018 | ..... G06Q 10/063112 |

OTHER PUBLICATIONS

Iqbal, Shamsi T. et al., "Disruption and Recovery of Computing Tasks: Field Study, Analysis, and Directions," Proceedings of the SIGCHI Conference on Human Factors in Computing Systems, 2007, pp. 677-686. (Year: 2007).*

(Continued)

*Primary Examiner* — Hafiz A Kassim
(74) *Attorney, Agent, or Firm* — KRAGULJAC LAW GROUP, LLC

(57) ABSTRACT

Methods, computer systems, and computer storage media are provided for utilizing system diagnostics focused in areas of disruption to improve inventory and workforce management in a revenue cycle management system. Inventory input is received from a revenue cycle management system. The inventory input includes inventory in the revenue cycle management system, types of claims in the inventory, pair agreements of the claims, and a length of time the claims have been in the inventory. Workforce input is also received from the revenue cycle management system. The workforce input includes experience, type of education or technical training, specialty, and outcomes corresponding to a workforce of the client. A portion of the inventory is automatically assigned to an associate of the workforce. The portion of the inventory tailored to the associate based on the inventory input and the workforce input.

19 Claims, 19 Drawing Sheets

(51) Int. Cl.
  *G06N 5/04* (2023.01)
  *G06Q 10/0639* (2023.01)
  *G06Q 10/0631* (2023.01)
  *G06Q 10/0637* (2023.01)
  *G06Q 10/105* (2023.01)

(52) U.S. Cl.
  CPC ........... *G06Q 10/06398* (2013.01); *G06Q 10/063112* (2013.01); *G06Q 10/105* (2013.01)

(56) References Cited

U.S. PATENT DOCUMENTS

| | | | | |
|---|---|---|---|---|
| 2003/0191665 A1* | 10/2003 | Fitzgerald | G16H 50/20 | 705/2 |
| 2004/0267770 A1* | 12/2004 | Lee | G06F 16/2465 | |
| 2006/0242154 A1* | 10/2006 | Rawat | G06F 16/168 | |
| 2007/0288367 A1* | 12/2007 | Krishnamoorthy | G06Q 20/102 | 705/40 |
| 2009/0132331 A1* | 5/2009 | Cartledge | G06Q 10/10 | 705/7.27 |
| 2010/0256985 A1* | 10/2010 | Nix | G16H 15/00 | 715/764 |
| 2011/0161378 A1* | 6/2011 | Williamson | G06F 16/9027 | 707/812 |
| 2011/0218845 A1* | 9/2011 | Medina | G06Q 30/0257 | 705/14.55 |
| 2013/0035977 A1* | 2/2013 | Fernandez | G06Q 10/00 | 705/7.27 |
| 2014/0052680 A1* | 2/2014 | Nitz | G06N 5/04 | 706/46 |
| 2014/0108038 A1* | 4/2014 | Lipsky | G06Q 30/04 | 705/2 |
| 2014/0278512 A1* | 9/2014 | Young | G16H 10/60 | 705/2 |
| 2015/0067699 A1* | 3/2015 | Plotkin | G06F 9/48 | 718/107 |
| 2015/0317337 A1* | 11/2015 | Edgar | G16H 50/70 | 707/751 |
| 2016/0019357 A1* | 1/2016 | Marzula | G06Q 10/10 | 705/2 |
| 2016/0180030 A1* | 6/2016 | Gunawardena | G06Q 40/12 | 705/2 |
| 2017/0061356 A1* | 3/2017 | Haas | G06Q 10/06316 | |
| 2021/0202077 A1 | 7/2021 | Streich et al. | | |

OTHER PUBLICATIONS

Tanya Bahl et al., "Enhancement of Revenue Cycle Management: Case In Change Management," Master of Health Administration, BDS, Panjab University, India, 2016. (Year: 2016).*

United States Patent & Trademark Office (USPTO), First Action Interview Pilot Program Pre-Interview Communication issued in U.S. Appl. No. 16/998,133, (filed Aug. 20, 2020) having a Notification Date of Mar. 29, 2023 (5 pgs).

* cited by examiner

| Disruption | Description | Count | Balance |
|---|---|---|---|
| | 304 — Top Areas of Disruption  306 | | 308 |
| Edit Failure | Review Claim | 121 | $453,836 |
| Denial | 18 – Duplicate claim/service | 23 | $8,234 |
| Denial | 9 – Dx inconsistent with patient's age | 19 | $6,465 |
| Bill Suppression | Pending Registration Modification | 5 | $4,084 |
| Denial | N301 – Invalid procedure date(s) | 1 | $78,739 |
| Denial | 484 – Resubmit with Medical Records & Office No | 3 | $1,030 |
| Edit Failure | Admission type or source missing | 3 | $810 |
| Denial | 66BC – Additional info requested from Provider | 3 | $691 |
| Denial | M51 – Incmplt/invld proc cd or rate | 1 | $407,160 |
| Denial | M45 – Incomplete/invalid occurrence cds/dates | 1 | $78,739 |

FIG. 3

| Workstream | Category | Summary | Action Items | Impact |
|---|---|---|---|---|
| Foundational* | Clean-Up | Manual Charge | These are charges that were manually entered, so they are not a part of a streamlined clinical workflow | 240 charges at $3500 (past 24 hours) |
| Foundational* | Clean-Up | Encounter Combine Failures | Financial encounters that failed to combine. Need to log a ticket to support to run clean up script. | Encounter Combine Failures |
| Foundational* | Clean-Up | Person Combine Failures | Combine accounts that failed even though a clinical combine was successful. Need to log a ticket to support to run clean up script. | Person Combine Failures |
| Foundational* | Clean-Up | Pending Reg Mods | Encounter modification failure. Need to run clean up script. | Pending Reg Mods |
| Foundational* | Clean-Up | $0Scernio2 | Incomplete primary balance with no charges. Balance was created on a charge posting but either the charges were for $0 or they were later reversed leaving us with a $0 balance. | $0Scernio2 |
| Foundational* | Clean-Up/ Workflow | Voided Benefit Orders | Need to run VBO query to identify encounters that need to be cleaned up. Cerner to provide results to the client | Voided Benefit Orders |

FIG. 7

| Workstream | Category | Summary | Action Items | Impact |
|---|---|---|---|---|
| Foundational* | Clean-Up | Offsetting Balances | Returns all non $0 offsetting balances on $0 patient encounters | 7 instances |
| Foundational* | Review | Standard Delay by Billing Entity | Returns Standard Delay breakdown by Billing Entity | 6 out of 6 billing entity and encounter type combinations have standard delay exceeding model recommendations |

FIG. 8

| Workstream | Category | Summary | Action Items | Count | Balance |
|---|---|---|---|---|---|
| Edit Failure | Workflow | Review Claim | This validation edit is stopping every claim for a specific facility. Explore options to add required information to the claim automatically instead of having to review each individual claim. | 121 | $453k |

FIG. 9

| Workstream | Category | Summary | Action Items | Count | Balance |
|---|---|---|---|---|---|
| Denial Management | Workflow | 9 – Dx inconsistent with patient's age | Review workflow and communication with providers on diagnosis, procedure alignment, and patient demographics.<br><br>Resolution: Review coding guidelines and diagnosis, procedure alignment, and patient demographics according to CMS regulations.<br><br>Hours: Client Specific | 19 Claims | $6.5k |

FIG. 11

| Workstream | Category | Summary | Action Items | Count | Balance |
|---|---|---|---|---|---|
| Bill Suppression | Workflow | Pending Registration Modification | | 5 Encounters | $4k |

| Workstream | Category | Summary | Action Items | Count | Balance |
|---|---|---|---|---|---|
| | 1504 | 1506 | 1508 | 1510 | 1512 |
| Edit Failure | Build | Admission type or source missing | Review core code builder to ensure the appropriate outbound aliases are assigned to admit type/source values. Ensure all registration conversations have the admit type/source as a required field to ensure this information is captured during the registration. If this is the case of a change in encounter type, explore possibilities of a claim rule populating these values under specific conditions. | 3 | $810 |

| Workstream | Category | Summary | Action Items | Count | Balance |
|---|---|---|---|---|---|
| | 1604 | 1606 | 1608 | 1610 | 1612 |
| Denial Management | Workflow | 66BC — Additional info requested from Prov | Review and determine if work item can be created based on additional information from provider need to ensure the information is attached before the claim goes to the payer.<br><br>Hours: Client specific | 3 Claims | $691 |

| Workstream | Category | Summary | Action Items | Count | Balance |
|---|---|---|---|---|---|
| Denial Management | Configuration | M51 — Incmplt/invld proc cd or rate | Review build for remark codes posting as technical denials. Remark codes incorrectly posting as denials duplicate reporting, incorrectly increase denied balance, and count impact correct balances rolling.<br><br>Cerner Model Recommendation is setting M and N codes to information only as they do not process as a claim adjustment reason codes would and hold no transaction amount.<br><br>Resolution: This should be set to Information Only in order to avoid denial inflation. The dollar amount is also associated to another denial code. | 1 Claim | $407k |

FIG. 17

| Workstream | Category | Summary | Action Items | Count | Balance |
|---|---|---|---|---|---|
| Denial Management | Configuration | M45 – Incomplete/invalid occurrence cds/dates | Review build for remark codes posting as technical denials. Remark codes incorrectly posting as denials duplicate reporting, incorrectly increase denied balance, and could impact correct balances rolling.<br><br>Cerner Model Recommendation is setting M and N codes to information only as they do not process as a claim adjustment reason codes would and hold no transaction amount.<br><br>Resolution: This should be set to Information Only to avoid denial inflation. The dollar amount is also associated to another denial code. | 1 Claim | $78.7k |

FIG. 18

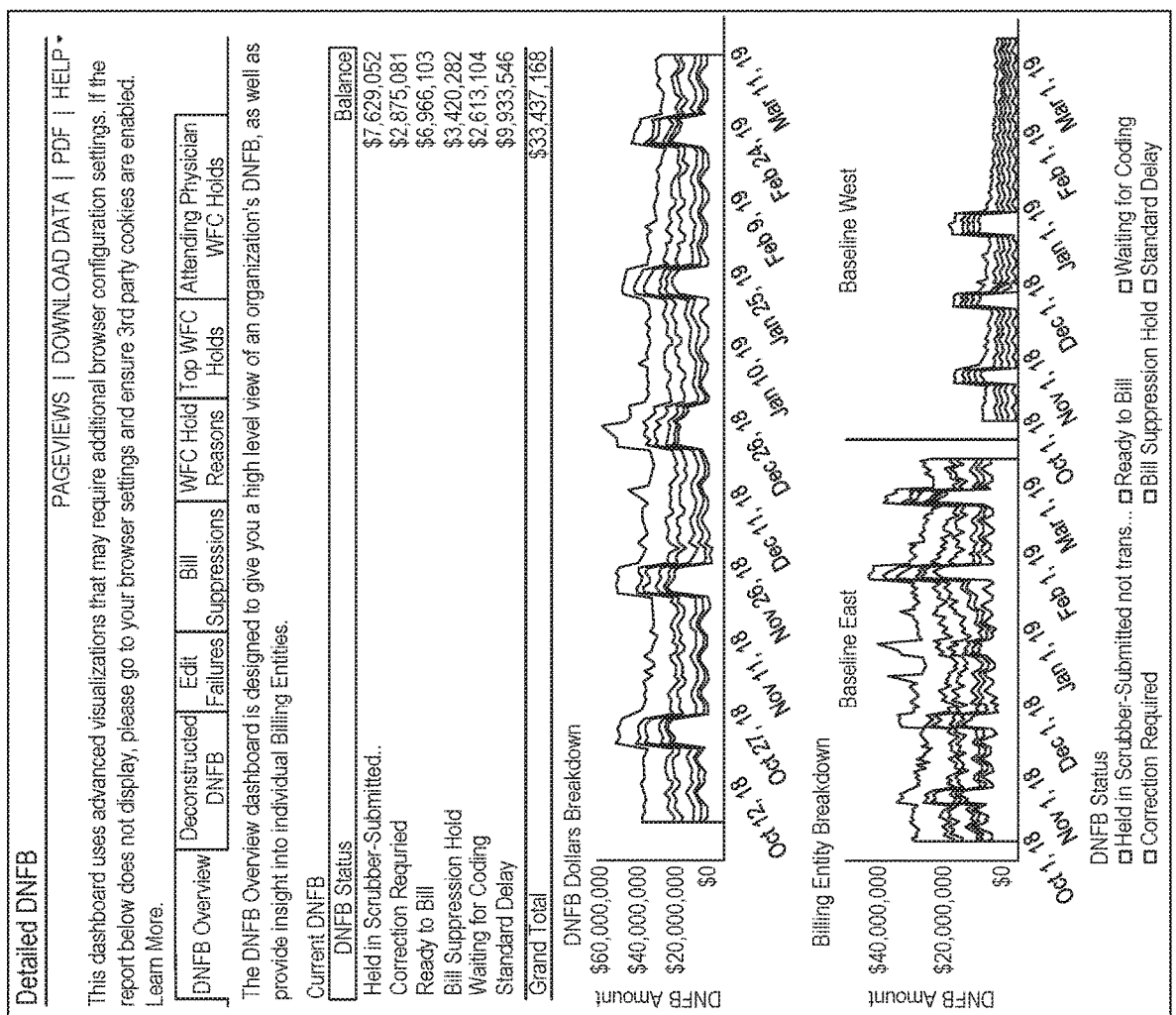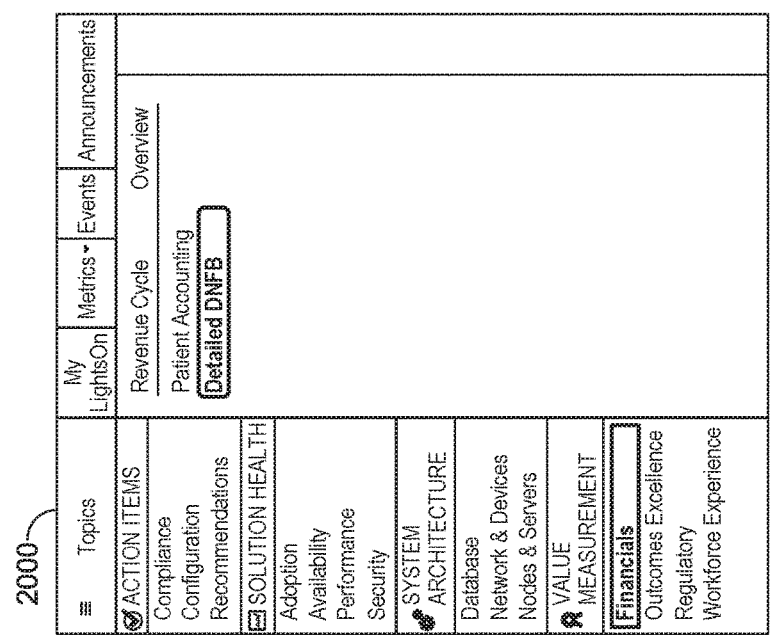
FIG. 20

REVENUE CYCLE WORKFORCE MANAGEMENT

BACKGROUND

Revenue cycle management is a financial process utilized by health care systems to track revenue derived from patient encounters. Health care systems typically utilize medical billing software to track patient encounters from registration through the final payment of a balance. The revenue cycle comprises many components, including preregistration, registration, charge capture, coding, claims submission, remittance processing, third-party follow, patient collections, utilization review, and the like. Any disruption during any component of the revenue cycle results in delayed or lost reimbursement. To address disruptions, current revenue cycle management systems require human intervention for each disruption which is often cost prohibitive. Moreover, health care systems struggle to collect all potential revenue and the workforce necessary to address disruptions is overwhelmed.

BRIEF SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

Embodiments of the present invention relate to leveraging diagnostic data to optimize revenue cycle management. More particularly, the present invention utilizes system diagnostics focused in areas of disruption to improve inventory and workforce management. Initially, diagnostic data is utilized to automatically identify disruptions in a revenue cycle management system across a plurality of clients. The disruptions are automatically ranked based on an impact to the revenue cycle management system and a time required to execute a correction for each disruption. A recommendation is provided for the client to execute the correction for each disruption.

Embodiments of the present invention relate to leveraging diagnostic data to optimize revenue cycle management. More particularly, the present invention utilizes system diagnostics focused in areas of disruption to improve inventory and workforce management. Initially, inventory input is received from a revenue cycle management system. The inventory input includes inventory in the revenue cycle management system, types of claims in the inventory, pair agreements of the claims, and a length of time the claims have been in the inventory. Workforce input is also received from the revenue cycle management system. The workforce input includes experience, type of education or technical training, specialty, and outcomes corresponding to a workforce of the client. A portion of the inventory is automatically assigned to an associate of the workforce. The portion of the inventory tailored to the associate based on the inventory input and the workforce input.

BRIEF DESCRIPTION OF THE SEVERAL VIEWS OF THE DRAWINGS

The present invention is described in detail below with reference to the attached drawing figures, wherein:

FIGS. 3-20 depict illustrative screen displays, in accordance with embodiments of the present invention;

DETAILED DESCRIPTION

Figure 1:
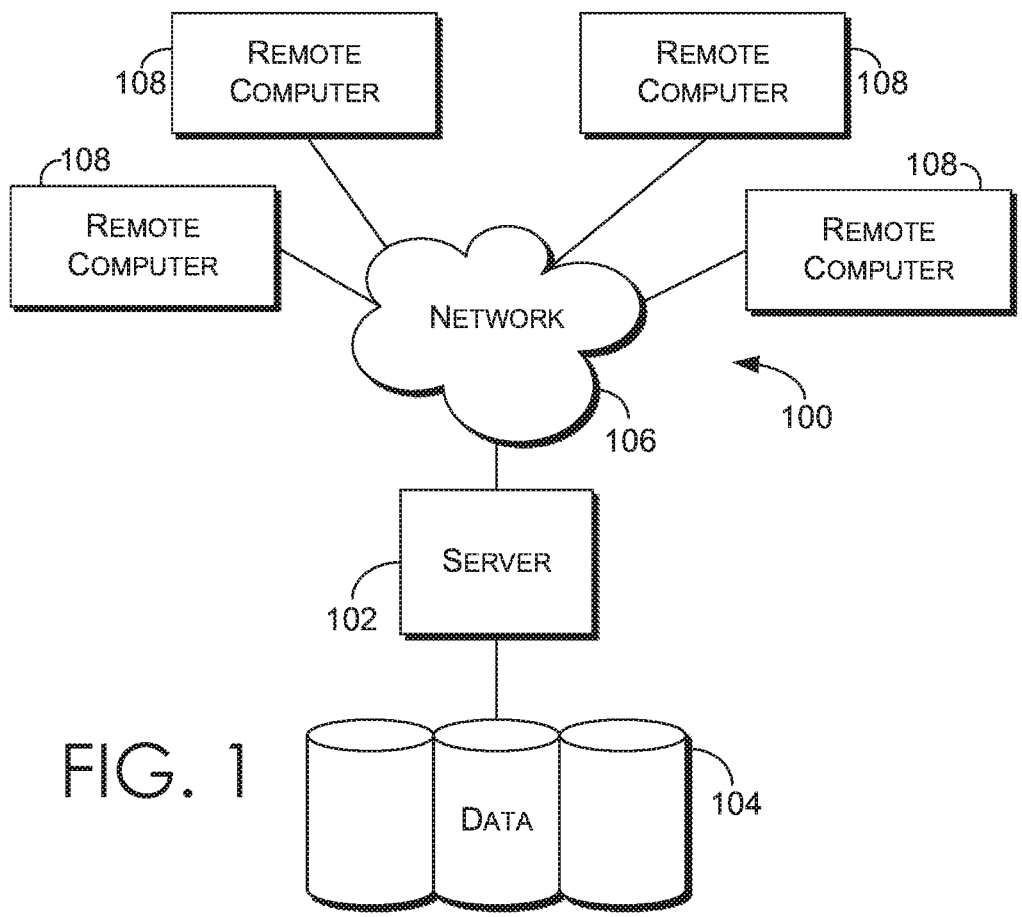
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

As noted in the Background, health care systems typically utilize medical billing software (e.g., revenue cycle systems) to track patient encounters from registration through the final payment of a balance. The revenue cycle comprises many components, including preregistration, registration, charge capture, coding, claims submission, remittance processing, third-party follow, patient collections, utilization review, and the like. Any disruption during any component of the revenue cycle results in delayed or lost reimbursement. To address disruptions, current revenue cycle management systems require human intervention for each disruption which is often cost prohibitive. Moreover, health care systems struggle to collect all potential revenue and the workforce necessary to address disruptions is overwhelmed.

Some embodiments of the present invention relate to leveraging diagnostic data to optimize inventory management in a revenue cycle management system. To do so, diagnostic data is initially utilized to automatically identify disruptions in a revenue cycle management system across a plurality of clients. The disruptions are automatically ranked based on an impact to the revenue cycle management system and a time required to execute a correction for each disruption. A recommendation is provided for the client to execute the correction for each disruption.

Some embodiments of the present invention relate to leveraging diagnostic data to optimize workforce management in a revenue cycle management system. To do so, inventory input is initially received from a revenue cycle management system. The inventory input includes inventory in the revenue cycle management system, types of claims in the inventory, pair agreements of the claims, and a length of time the claims have been in the inventory. Workforce input is also received from the revenue cycle management system.

The workforce input includes experience, type of education or technical training, specialty, and outcomes corresponding to a workforce of the client. A portion of the inventory is automatically assigned to an associate of the workforce. The portion of the inventory tailored to the associate based on the inventory input and the workforce input.

Accordingly, in one aspect, an embodiment is directed to one or more computer storage media having computer-executable instructions embodied thereon that, when executed by a computer, causes the computer to perform operations. The operations include utilizing diagnostic data, automatically identifying disruptions in a revenue cycle management system across a plurality of clients. The operations also include automatically ranking the disruptions for a client of the plurality of clients based on an impact to the revenue cycle management system and a time required to execute a correction for each disruption. The operations further include providing a recommendation for the client to execute the correction for each disruption.

In another aspect of the invention, an embodiment of the present invention is directed to a computerized method. The method includes utilizing diagnostic data, automatically identifying disruptions in a revenue cycle management system across a plurality of clients. The method also includes automatically ranking the disruptions for a client of the plurality of clients based on an impact to the revenue cycle management system and a time required to execute a correction for each disruption. The disruptions include suppressions, edit failures, and denials and the correction including one or more of process design, configuration, or change in workflow. The method further comprises providing a recommendation for the client to execute the correction for each disruption.

In a further aspect, an embodiment is directed to a computerized system that includes one or more processors and a non-transitory computer storage medium storing computer-useable instructions that, when used by the one or more processors, cause the one or more processors to: utilizing diagnostic data, automatically identify disruptions in a revenue cycle management system across a plurality of clients; automatically rank the disruptions for a client of the plurality of clients based on an impact to the revenue cycle management system and a time required to execute a correction for each disruption, the disruptions including suppressions, edit failures, and denials and the correction including one or more of process design, configuration, or change in workflow; and provide a recommendation for the client to execute the correction for each disruption.

In one aspect, an embodiment is directed to one or more computer storage media having computer-executable instructions embodied thereon that, when executed by a computer, causes the computer to perform operations. The operations include receiving inventory input from a revenue cycle management system. The inventory input includes inventory in the revenue cycle management system, types of claims in the inventory, pair agreements of the claims, and a length of time the claims have been in the inventory. The operations also include receiving workforce input from the revenue cycle management system. The workforce input includes experience, type of education or technical training, specialty, and outcomes corresponding to a workforce of the client. The operations further include automatically assigning a portion of the inventory to an associate of the workforce. The portion of the inventory is tailored to the associate based on the inventory input and the workforce input.

In another aspect of the invention, an embodiment of the present invention is directed to a computerized method. The method includes receiving inventory input from a revenue cycle management system. The inventory input includes inventory in the revenue cycle management system, types of claims in the inventory, pair agreements of the claims, and a length of time the claims have been in the inventory. The method also includes receiving workforce input from the revenue cycle management system, the workforce input including experience, type of education or technical training, specialty, and outcomes corresponding to a workforce of the client. The method further includes automatically assigning a portion of the inventory to an associate of the workforce. The portion of the inventory is tailored to the associate based on the inventory input and the workforce input. The method also includes receiving audit information for the associate corresponding to performance of the associate within the revenue cycle management system. The method further includes automatically scaling up or down the portion of the inventory assigned to the associate based on the audit information.

In a further aspect, an embodiment is directed to a computerized system that includes one or more processors and a non-transitory computer storage medium storing computer-useable instructions that, when used by the one or more processors, cause the one or more processors to: receive inventory input from a revenue cycle management system, the inventory input including inventory in the revenue cycle management system, types of claims in the inventory, pair agreements of the claims, and a length of time the claims have been in the inventory; receive workforce input from the revenue cycle management system, the workforce input including experience, type of education or technical training, specialty, and outcomes corresponding to a workforce of the client; automatically assign a portion of the inventory to an associate of the workforce, the portion of the inventory tailored to the associate based on the inventory input and the workforce input; receive audit information for the associate corresponding to performance of the associate within the revenue cycle management system; and automatically scale up or down the portion of the inventory assigned to the associate based on the audit information.

An exemplary computing environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including data store 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of any of the above should also be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, ambulatory settings, medical billing and financial offices, hospital administration settings, home healthcare environments, clinicians' offices, Center for Disease Control, Centers for Medicare & Medicaid Services, World Health Organization, any governing body either foreign or domestic, Health Information Exchange, and any healthcare/government regulatory bodies not otherwise mentioned. Clinicians may comprise a treating physician or physicians; specialists such as intensivists, surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The devices can be personal digital assistants or other like devices.

Computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Figure 2:
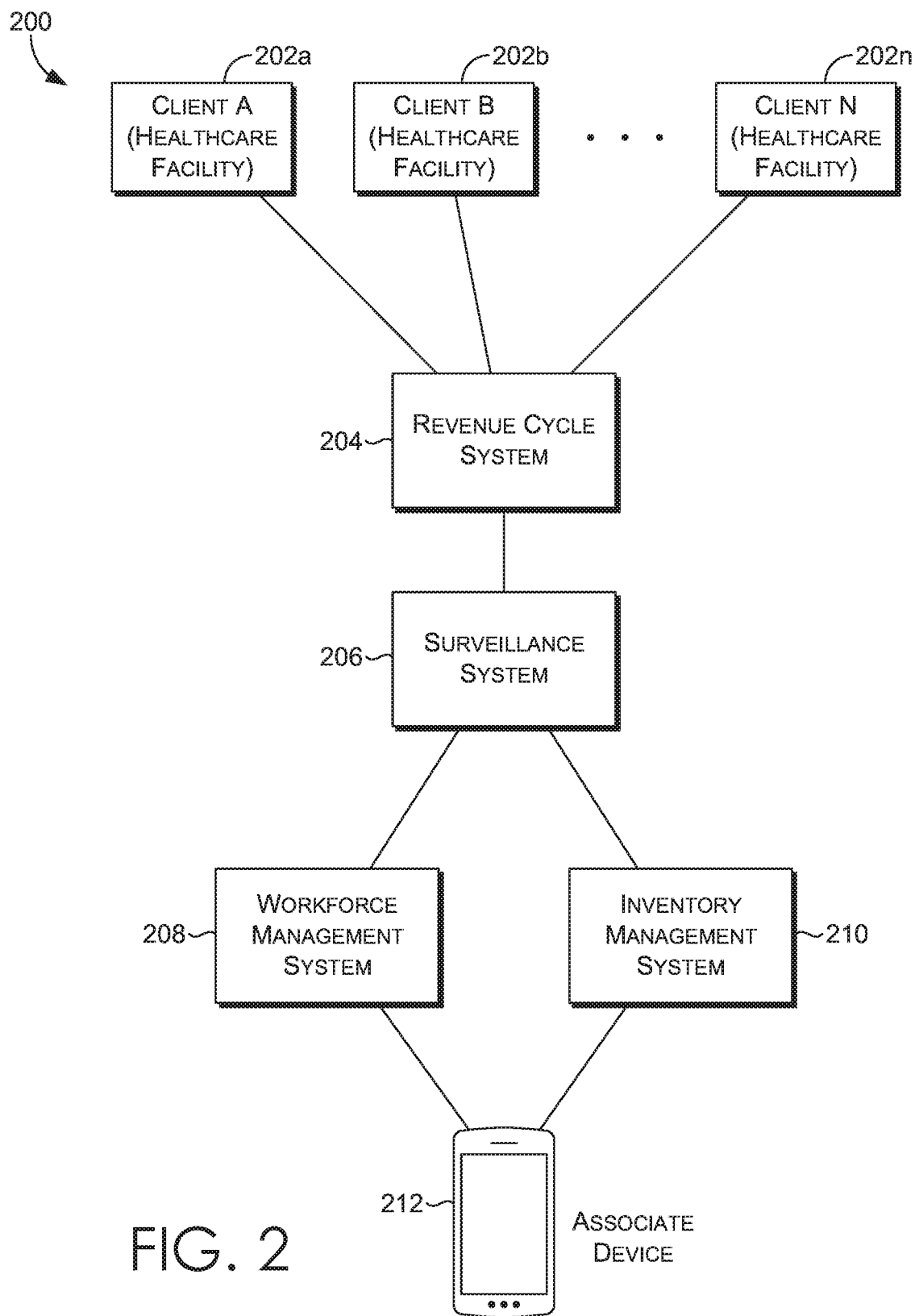
FIG. 2 is a block diagram of an exemplary system for optimizing inventory and workforce in a revenue cycle system, in accordance with an embodiment of the present invention.

Turning now to FIG. 2, an exemplary revenue cycle management system 200 is depicted suitable for use in implementing embodiments of the present invention. The revenue cycle management system 200 is merely an example of one suitable computing system environment and is not intended to suggest any limitation as to the scope of use or functionality of embodiments of the present invention. Neither should the revenue cycle management system 200 be interpreted as having any dependency or requirement related to any single module/component or combination of modules/components illustrated therein.

The revenue cycle management system 200 includes healthcare facilities 202A-202N, revenue cycle system 204, surveillance system 206, workforce management system 208, inventory management system 210, and associate device 212, all in communication with one another via a network. The network may include, without limitation, one or more secure local area networks (LANs) or wide area networks (WANs). The network may be a secure network associated with a facility such as a healthcare facility. The secure network may require that a user log in and be authenticated in order to send and/or receive information over the network.

The components/modules illustrated in FIG. 2 are exemplary in nature and in number and should not be construed as limiting. Any number of components/modules may be employed to achieve the desired functionality within the scope of embodiments hereof. Further, components/modules may be located on any number of servers. By way of example only, revenue cycle system 204, the surveillance system 206, the workforce management system 208, and/or the inventory management system 210 might reside on a server, cluster of servers, or a computing device remote from one or more of the remaining components. Although illustrated as separate systems, revenue cycle system 204, the surveillance system 206, the workforce management system 208, and/or the inventory management system 210, the functionality provided by each of these components might be provided as a single component/module. The single unit depictions are meant for clarity, not to limit the scope of embodiments in any form.

Components of the revenue cycle management system 200 may include a processing unit, internal system memory, and a suitable system bus for coupling various system components, including one or more data stores for storing information (e.g., files and metadata associated therewith). Components of the revenue cycle management system 200 typically includes, or has access to, a variety of computer-readable media.

It should be understood that this and other arrangements described herein are set forth only as examples. Other arrangements and elements (e.g., machines, interfaces, functions, orders, and groupings of functions, etc.) can be used in addition to or instead of those shown, and some elements may be omitted altogether. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

Each of Client A 202a, Client B 202b . . . Client N 202n includes or has access to infrastructure that is capable of receiving and storing information for use by, for example, revenue cycle system 204, surveillance system 206, workforce management system 208, or inventory management system 210. The information received and stored in association with each of Client A 202a, Client B 202b . . . Client N 202n may comprise general information used by revenue cycle system 204, surveillance system 206, workforce management system 208, or inventory management system 210. Each of Client A 202a, Client B 202b . . . Client N 202n may receive data from other systems (e.g., disparate healthcare systems), which may include any number or type of medical devices that may be utilized to provide or measure patient care to a patient.

Each of Client A 202a, Client B 202b . . . Client N 202n includes or has access to infrastructure that is capable of storing electronic health records (EHRs) of patients associated with Client A 202a, Client B 202b . . . Client N 202n. EHRs may comprise electronic clinical documents such as images, clinical notes, orders, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, alert history, culture results, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information. In some embodiments, Client A 202a, Client B 202b . . . Client N 202n may receive data from health information exchanges ("HIEs"), personal health records ("PHRs"), patient claims, and other health records associated with a patient. Although described with respect to healthcare information, it is contemplated Client A 202a, Client B 202b . . . Client N 202n may receive any type of records or information received from other systems, which may include any number or type of devices that may be utilized to provide or measure any data, that may benefit from workforce or inventory management.

Associate device 212 may be any type of computing device used within a healthcare facility or as part of the claims processing process to receive, display, and send information to another user or system. Associate device 212 may be capable of communicating via the network with Client A 202a, Client B 202b . . . Client N 202n (or corresponding systems of Client A 202a, Client B 202b . . . Client N 202n), revenue cycle system 204, surveillance system 206, workforce management system 208, or inventory management system 210. Such devices may include any type of mobile and portable devices including cellular telephones, personal digital assistants, tablet PCs, smart phones, and the like.

Associate device 212 is configured to display information to an associate via a display. The information may include communications initiated by and/or received by workforce management system 208 or inventory management system 210. Embodiments are not intended to be limited to visual display but rather may also include audio presentation, visual presentation, combined audio/visual presentation, and the like.

Generally, the revenue cycle system 204 is configured to track patient encounters for a client (e.g., Client A 202a) from preregistration through the final payment of a balance. For example, the revenue cycle system 204 tracks and collects data for patient encounters for each Client A 202a, Client B 202b . . . Client N 202n at preregistration, registration, charge capture, coding, claims submission, remittance processing, third-party follow, patient collections, utilization review, and the like. Although the revenue cycle system 204 is depicted as a single system, it is contemplated that each Client A 202a, Client B 202b . . . Client N 202n may utilize a different revenue cycle system 204.

Surveillance system 206 is generally configured to collect and analyze data maintained by the revenue cycle system 204. For example, surveillance system 206 may monitor data corresponding to the inventory of the revenue cycle system 204 or to the workforce that provides support to the revenue cycle system 204. In some embodiments, the data may include items such as charges, payments, adjustments, net change in A/R, average daily balance, A/R balance, A/R days, A/R greater than ninety days as a dollar amount, A/R greater than ninety days as a percentage, DNFB dollar amount, and DNFB days. Surveillance system analyzes the data and may identify disruptions in the revenue cycle system such as edit failures, denial management, and bill suppressions and corrections to correct the disruptions.

The surveillance system 206 may be configured to analyze a particular data point within the revenue cycle inventory (e.g., DNFB process) and identify and rank disruptions. In embodiments, the surveillance system 206 may collect and analyze data within a plurality of revenue cycle systems and identify and rank disruptions that may be system wide disruptions and not specific to any individual client.

Workforce management system 208 is generally configured to receive workforce input from the revenue cycle system 204 that can be utilized to identify and recommend a particular associate of the workforce to execute a correction for a disruption. The workforce input includes experience, type of education or technical training, specialty, and outcomes (e.g., audit information) corresponding to a workforce of the client. In some embodiments, the workforce management system 208 may assign a portion of the revenue cycle inventory to the associate. Based on receiving audit information corresponding to the associate, the workforce management system 208 may automatically scale up or down the portion of the inventory assigned to the associate.

Inventory management system 210 is generally configured to receive inventory input from revenue cycle system 204 that can be utilized to identify and recommend a particular correction to execute for a disruption. The inventory input includes inventory in the revenue cycle system, types of claims in the inventory, pair agreements of the claims, and a length of time the claims have been in the inventory. The recommendation may be based on a particular disruption or a volume of the disruption. The corrections may include process design, configuration, or a change in workflow. Moreover, the inventory management system 210 may provide information corresponding to disruptions and corrections in an interactive user interface.

With reference to FIGS. 3-20, illustrative screen displays 300, 400, 500 ... 2000 of embodiments of the present invention are shown. It is understood that each of the illustrative screen displays are connected logically, such that they comprise a user interface designed for providing revenue cycle inventory management and/or revenue cycle workforce management. The screen displays may appear in any order and with any number of screen displays, without regard to whether the screen display is described or depicted herein. The screen displays provide tools that enable reusable analytics in accordance with embodiments of the present invention.

Referring initially to FIG. 3, display 300 depicts the top areas of disruption. As illustrated the disruptions may correspond to suppressions, edit failures, and denials. The display 300 provides a description 304 for each disruption 302, a count 306 for each disruption 302, and a balance 308 (i.e., the total cost) for each disruption 302.

Figure 4A:
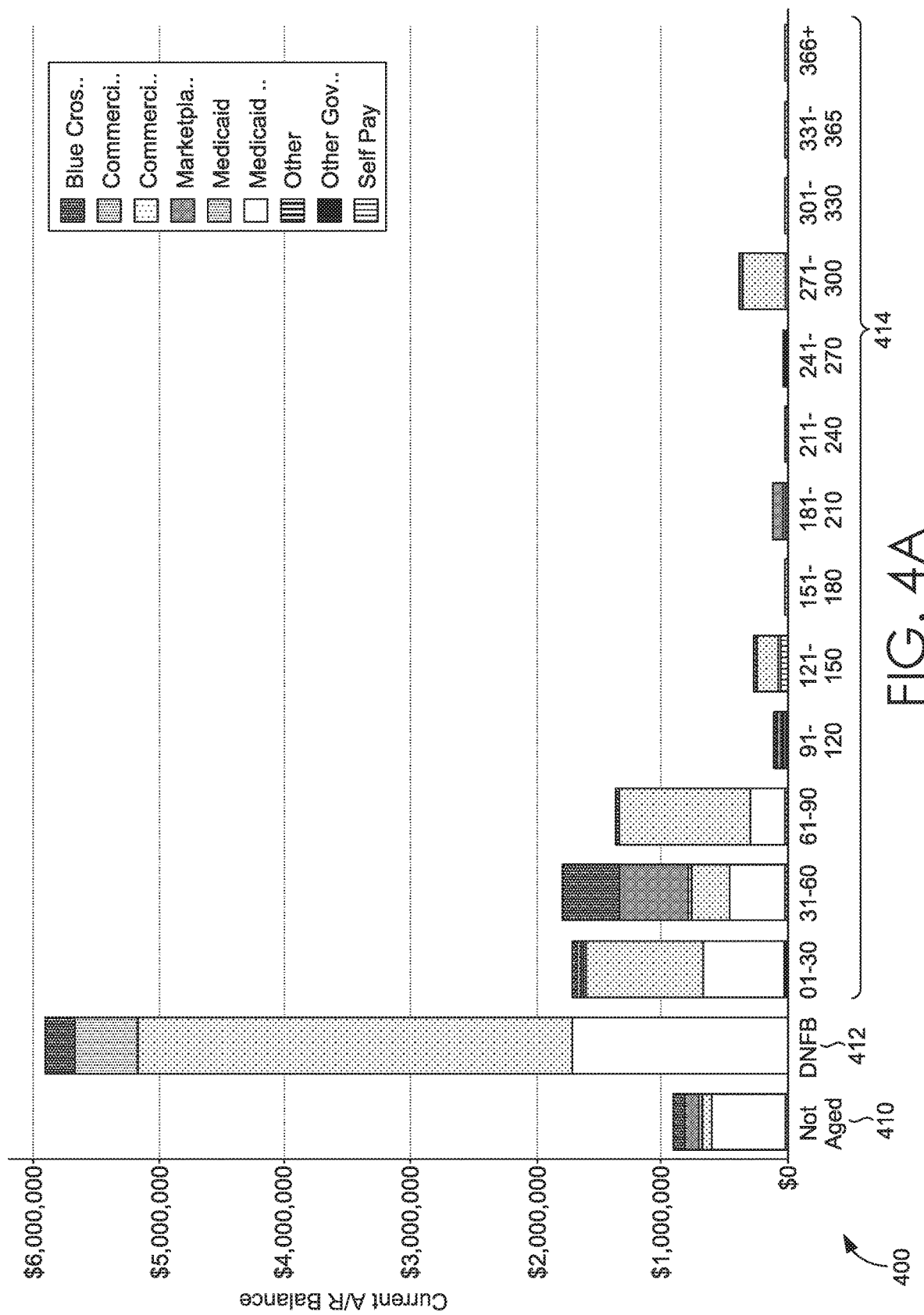
Figure 4B:
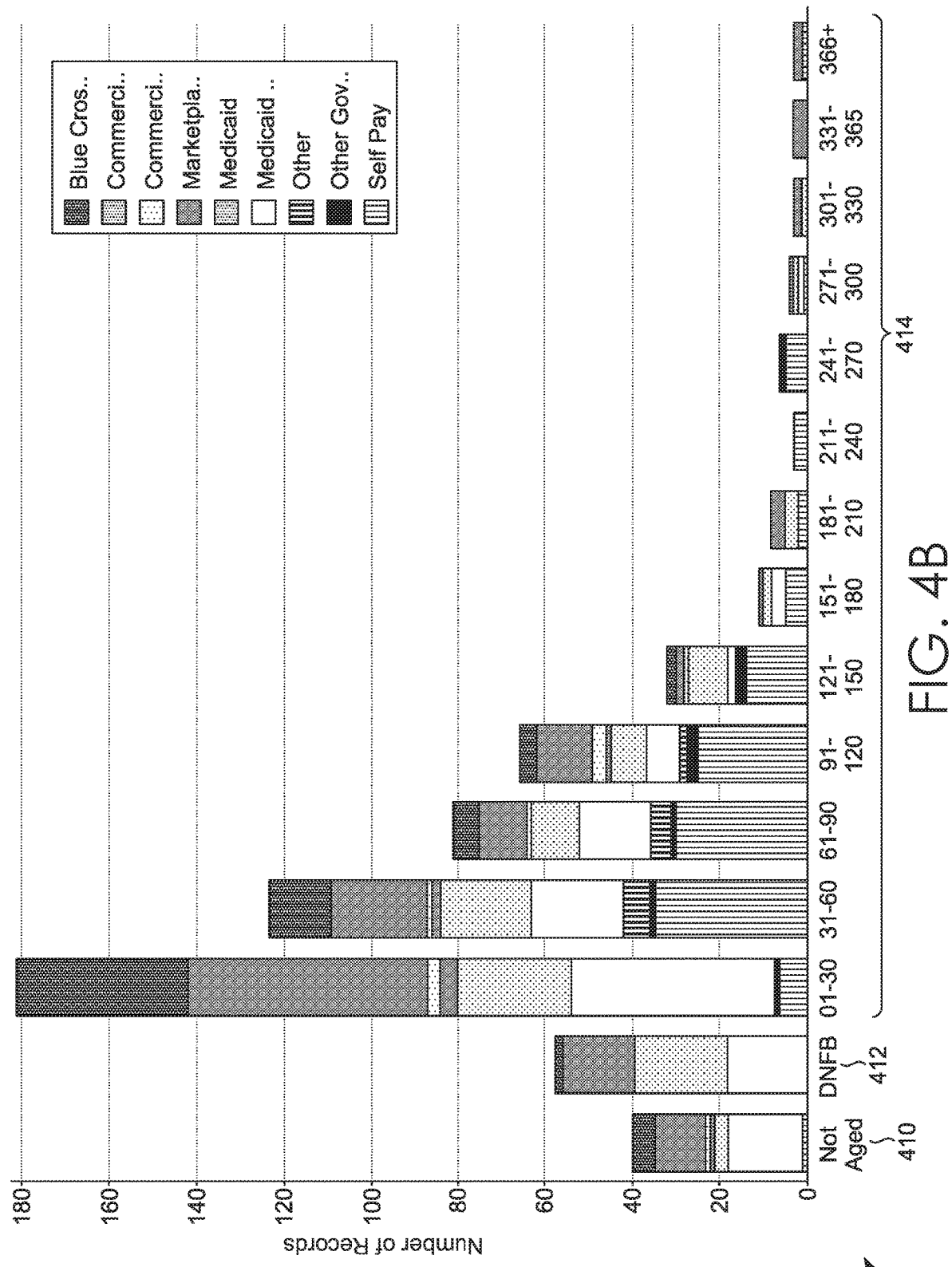

In FIGS. 4A and 4B, displays 400, 402 illustrate a chart that shows the age for a by accounts receivable (A/R) balance and count of records, respectively. In FIG. 4A, the display 400 distinguishes between payers such that a client can readily identify the delay for a count of records for each payer. For example, the A/R balance for claims that are not currently under any delay are illustrated by the "Not Aged" column 410. Similarly, the A/R balance for claims that have a discharged not final billed (DNFB) status are displayed in the "DNFB" column 412. Likewise, the A/R balance for claims with delay counts are illustrated in separate columns in increments of thirty days 414.

In FIG. 4B, display 402 also distinguishes between payers such that a client can readily identify the delay for a count of records for each payer. For example, a count of claims that are not currently under any delay are illustrated by the "Not Aged" column 410. Similarly, a count of claims that have a discharged not final billed (DNFB) status are displayed in the "DNFB" column 412. Likewise, a count of claims with delay counts are illustrated in separate columns in increments of thirty days 414.

Figure 5:
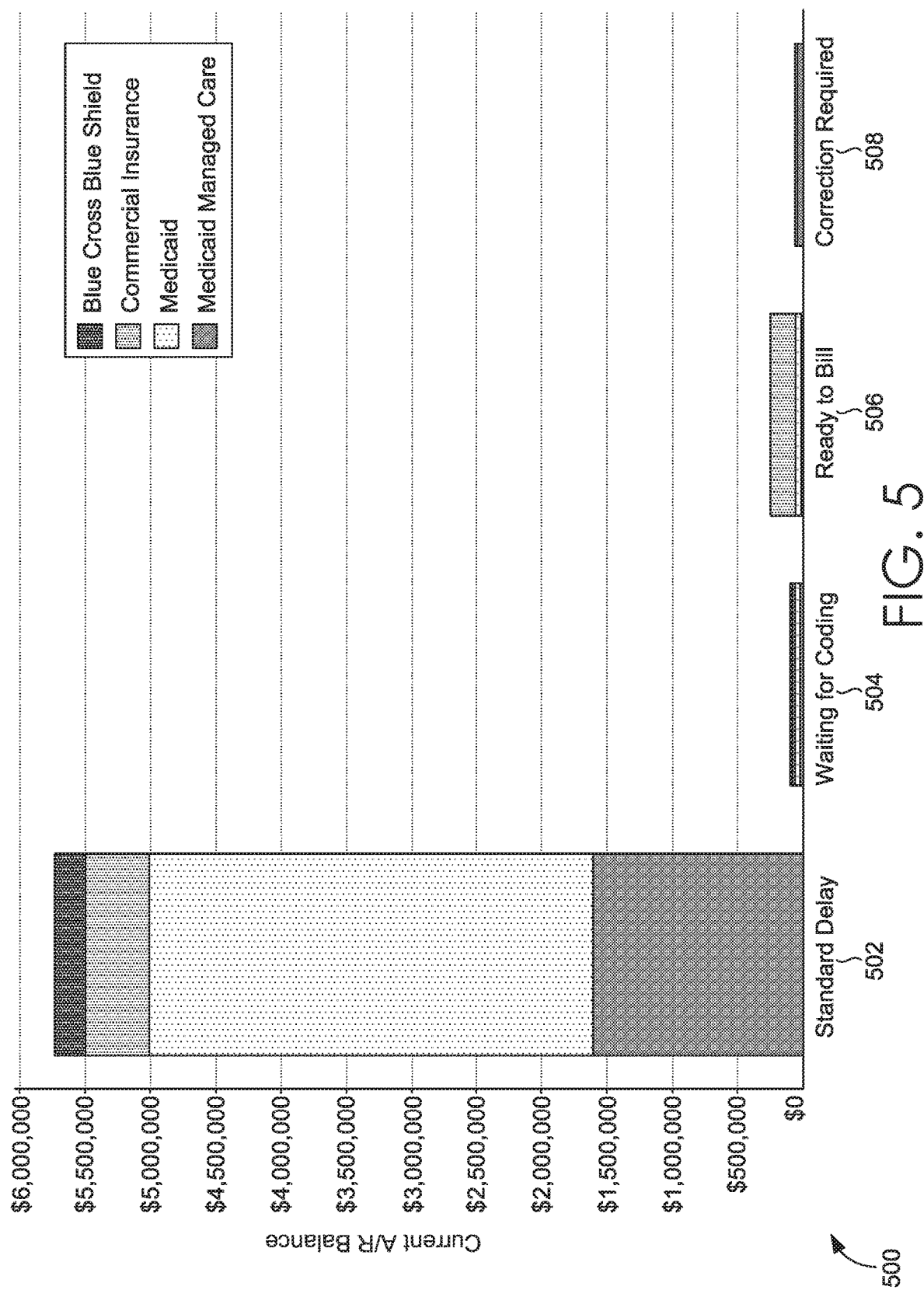

Referring to FIG. 5, display 500 illustrates a chart that shows the A/R balance for each DNFB reason (e.g., standard delay, waiting for coding, ready to bill, and correction required). In FIG. 5, the display 500 distinguishes between payers such that a client can readily identify the A/R balance for each payer for each DNFB reason. For example, the A/R balance for each payer for claims that are currently under standard delay are illustrated by the "Standard Delay" column 502. Similarly, the A/R balance for claims for each payer for claims that are currently waiting for coding are displayed in the "Waiting for Coding" column 504. Likewise, the A/R balance for claims for each payer for claims that are currently ready to bill are illustrated in a "Ready to Bill" column 506. Finally, the A/R balance for claims for each payer for claims that currently require correction are illustrated in a "Correction Required" column 508.

Figure 6:
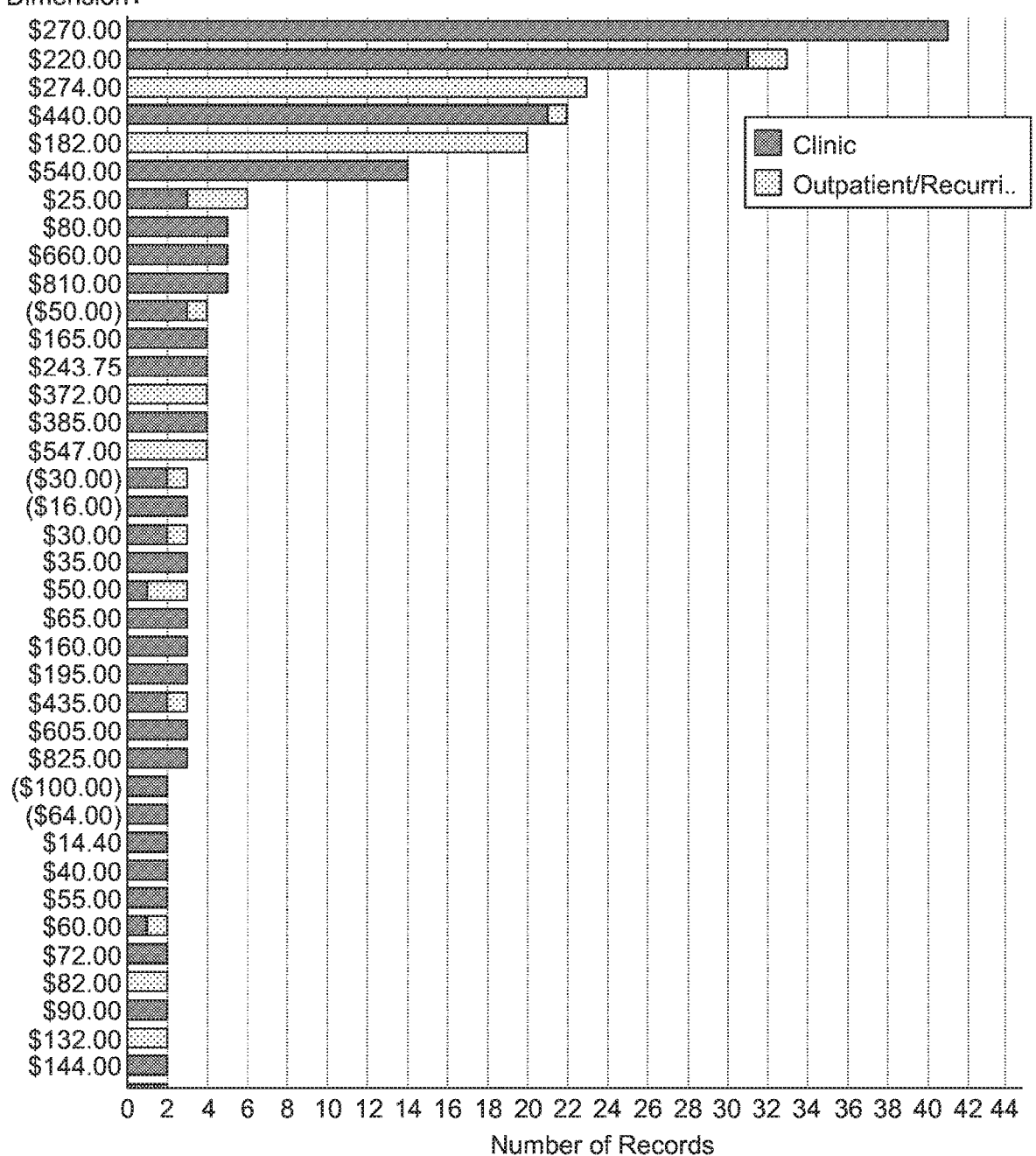
Figure 10:
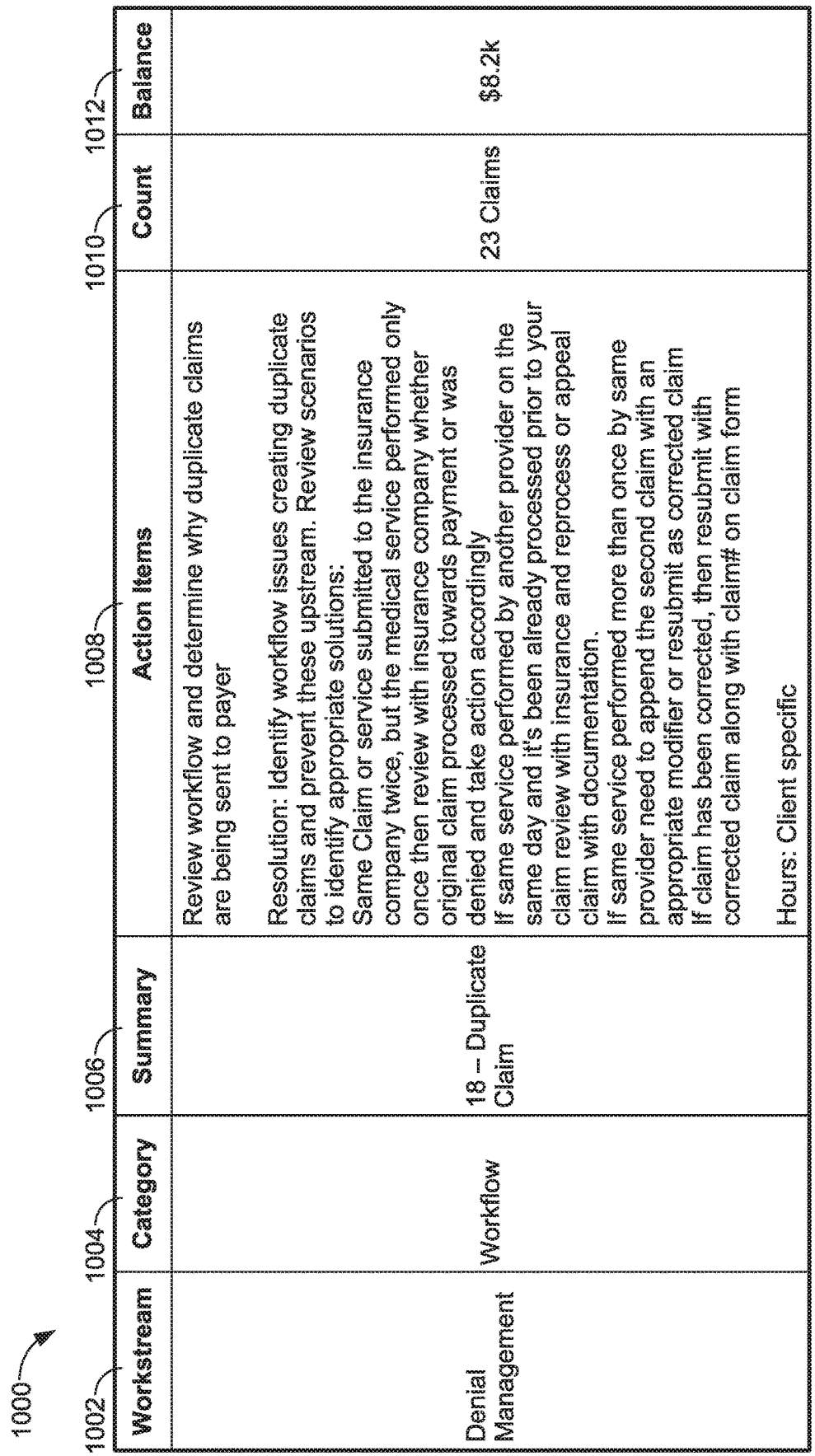
Figure 13:
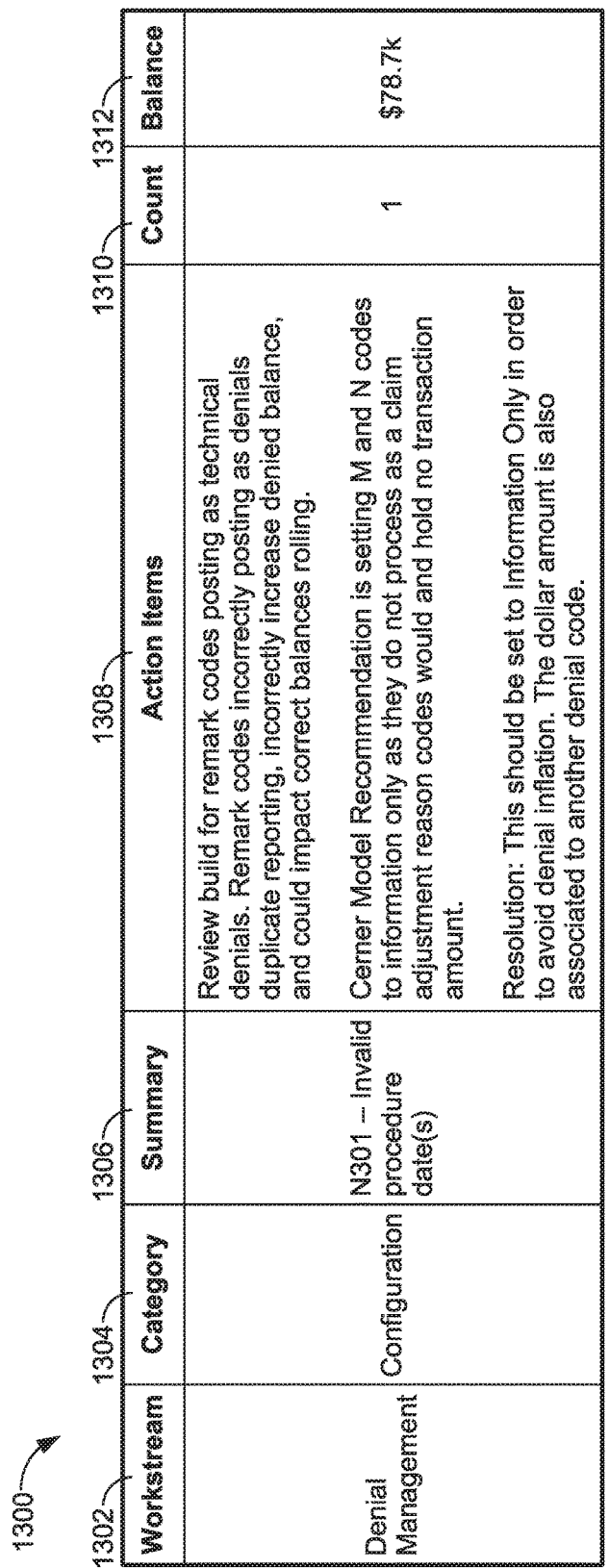
Figure 14:
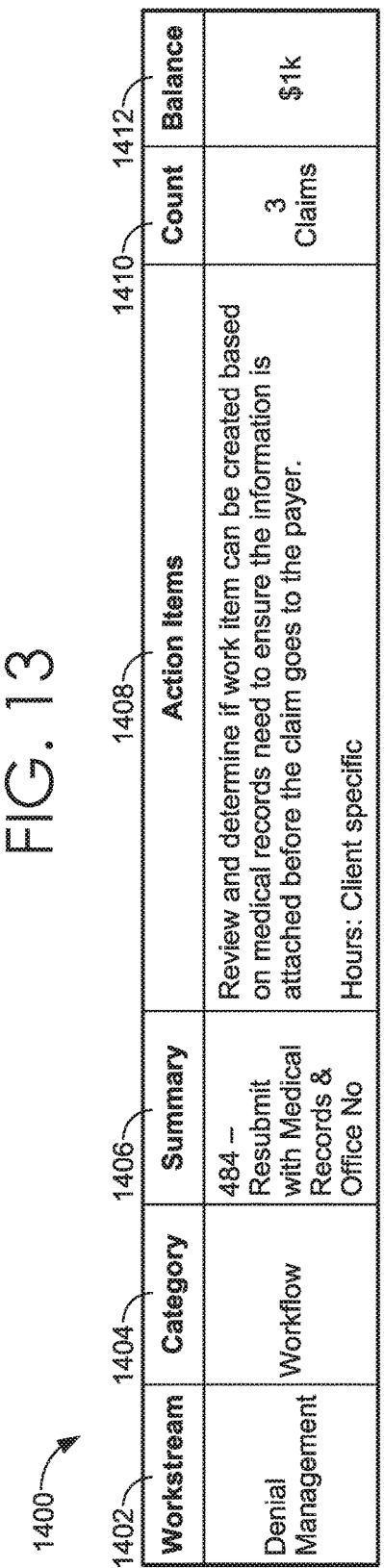

In FIG. 6, display 600 illustrates a number of records for similar A/R balance groupings. As illustrated, the display 600 distinguishes between encounter types. The encounter types may include clinic, inpatient, outpatient/recurring, or preregistration.

As shown in FIGS. 7-8, displays 700, 800 illustrate activity data audits that may be identified by a revenue cycle management system such as revenue cycle management system 200 of FIG. 2. As illustrated, displays 700 and 800 include columns that define the particular workstream 702, 802, category 704, 804, summary 706, 806, action items 708, 808, and impact for each activity 710, 810. For example, the workstream may include activities that refer to foundational items. As such, the categories may include clean-up, workflow, or review activities. The summary describes a short summary of the action item (e.g., manual charge, encounter combine failures, person combine failures, voided benefit orders, offsetting balances, standard delay by billing entity, review claim, etc.). The action items describe the activity and the process necessary to complete the activity. The impact illustrates the impact of each activity.

In FIGS. 9-18, displays 900-1800 illustrates disruptions that may be identified by a revenue cycle management system such as revenue cycle management system 200 of FIG. 2. The displays 900-1800 include columns that define the particular workstream 902, 1002 ... 1802, category 904, 1004 ... 1804, summary 906, 1006 ... 1806, action items 908, 1008 ... 1808, count 910, 1010 ... 1810, and balance 9012, 1012 ... 1812 for each disruption. For example, the workstream 902, 1002 ... 1802 may define the disruption as edit failures, denial management, and bill suppressions. Accordingly, the categories 904, 1004 ... 1804 may include workflow, configuration, or build solutions to address the disruptions. The summary 906, 1006 ... 1806 describes a short summary of the action item (e.g., manual charge, encounter combine failures, person combine failures, voided benefit orders, offsetting balances, standard delay by billing entity, review claim, etc.). The action items 908, 1008 . . . 1808 describe the disruption and the process necessary to correct the disruption. The count 910, 1010 . . . 1810 identifies the number of claims affected by a particular disruption. The balance 9012, 1012 . . . 1812 identifies the total outstanding corresponding to a particular disruption.

Figure 19:
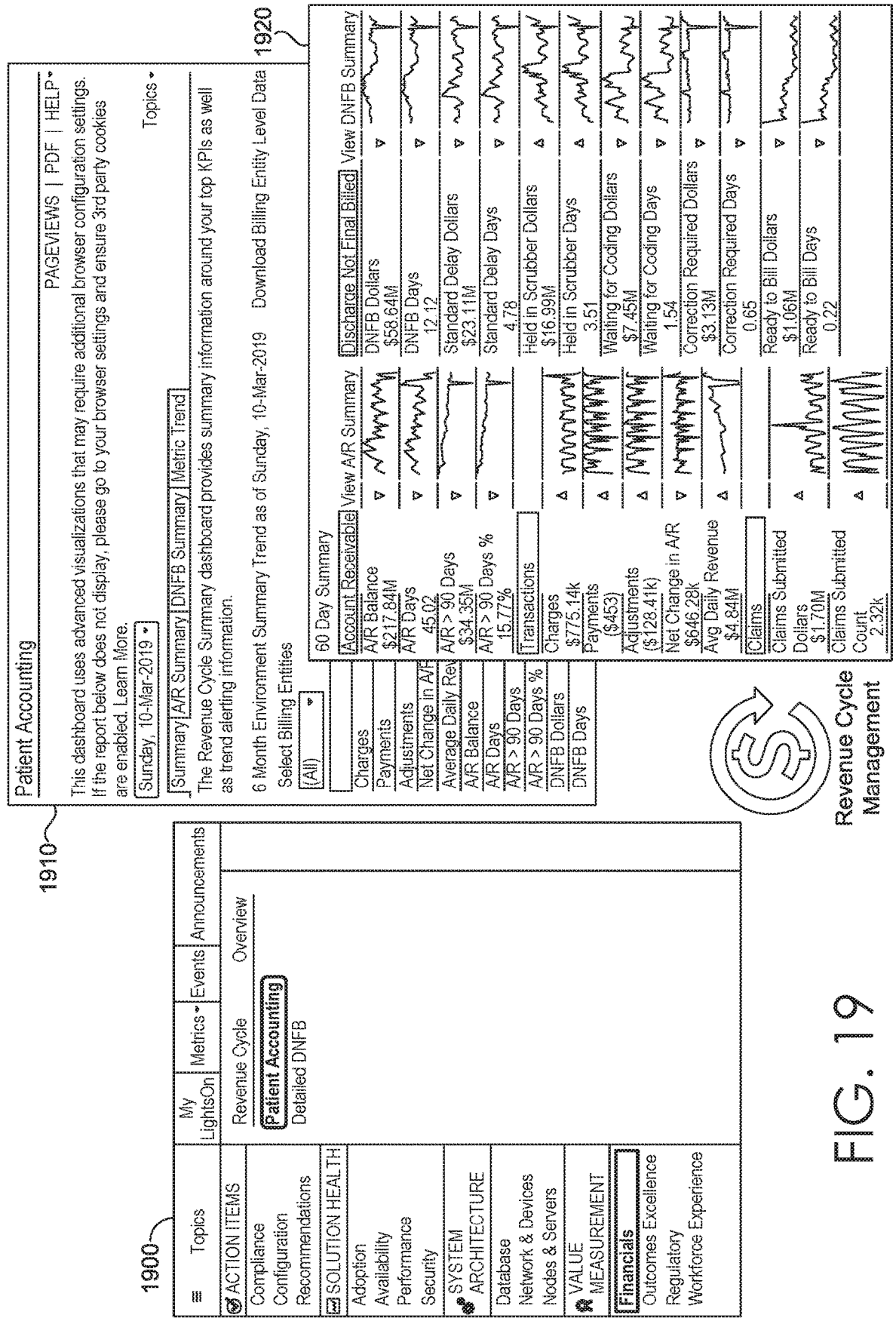

Referring now to FIG. 19, a dashboard 1900 is displayed. The dashboard 1900 enables a user to select the appropriate revenue cycle and topic. As illustrated, a user has selected the patient accounting revenue cycle with financials selected as the value measurement. As a result, a patient accounting dashboard 1910 is provided and enables the user to view summary information corresponding to key performance indicators (KPI) and trend alerting information. For example, the patient accounting dashboard 1910 may show KPIs such as charges, payments, adjustments, net change in A/R, average daily balance, A/R balance, A/R days, A/R greater than ninety days as a dollar amount, A/R greater than ninety days as a percentage, DNFB dollar amount, DNFB days, and the like. The trend alerting information may enable the user to view a historical average, a month-by-month average, and the like. A second display 1920 of the patient accounting dashboard 1910 enables the user to view a graphical summary of the information corresponding to key performance indicators (KPI) and trend alerting information shown in patient accounting dashboard 1910.

In FIG. 20, a dashboard 2000 (a similar dashboard to dashboard 1900 as shown in FIG. 19) is displayed. The dashboard 2000 enables a user to select the appropriate revenue cycle and topic. As illustrated, a user has selected the detailed DNFB revenue cycle with financials selected as the value measurement. As a result, a detailed DNFB dashboard 2010 is provided and enables the user to view a high level view of an organization's DNFB and insight into individual billing entities. For example, the detailed DNFB dashboard 2010 may a DNFB status and the balance of each status. The detailed DNFB dashboard 2010 may additionally show a DNFB dollar breakdown that illustrates the DNFB dollar amount over a period of time for each DNFB status. The detailed DNFB dashboard 2010 may also show a billing entity breakdown that illustrates a DNFB amount over a period of time for each DNFB status for each billing entity. Additional views may enable a user to view lower level views for each DNFB status, per disruption type, and the like.

Figure 21:
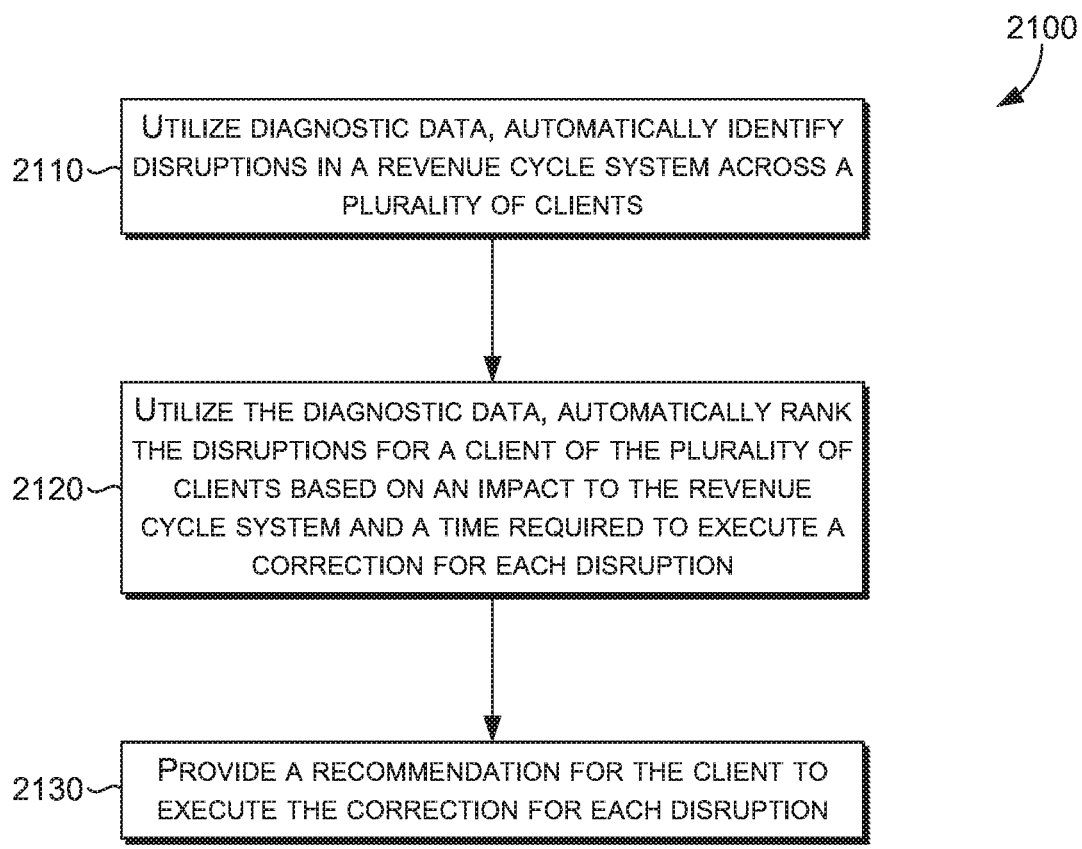
FIG. 21 is a flow diagram showing an exemplary method for optimizing inventory management in a revenue cycle management system, in accordance with various embodiments of the present invention.

Turning now to FIG. 21, a flow diagram is provided illustrating a method 2100 for providing revenue cycle inventory management, in accordance with an embodiment of the present invention. Method 2100 may be performed by any computing device (such as computing device described with respect to FIG. 1) with access to a revenue cycle management system (such as the one described with respect to FIG. 2) or by one or more components of the revenue cycle management system.

Initially, as shown at step 2110, diagnostic data is utilized to automatically identify disruptions in a revenue cycle system across a plurality of clients. The disruptions may include suppressions, edit failures, and denials.

At step 2120, the disruptions are automatically ranked for a client of the plurality of clients based on an impact to the revenue cycle system and a time required to execute a correction for each disruption. The correction may include one or more of process design, configuration, or change in workflow.

At step 2130, a recommendation is provided for the client to execute the correction for each disruption. The recommendation may be based on a particular disruption, a volume of the disruption, and training and experience of a workforce. In some embodiments, the recommendation identifies a particular associate of the workforce to execute the correction.

The recommendation may be based, at least in part, on inventory input for the client. The inventory input may include inventory in the revenue cycle system, types of claims in the inventory, pair agreements of the claims, and a length of time the claims have been in the inventory. The pair agreements of the claims may define how the client is reimbursed for each claim type.

In some embodiments, the recommendation is based, at least in part, on workforce input for the client. The workforce input may include experience, type of education or technical training, specialty, and outcomes corresponding to a workforce of the client.

In some embodiments, a portion of the inventory is assigned to an associate of the workforce. The portion of the inventory may be tailored to the associate based on the inventory input and the workforce input. Audit information may be received for the associate. The portion of the inventory assigned to the associate may be automatically scaled up or down based on the audit information.

In some embodiments, a dashboard is provided that identifies an overall count of disruptions in a client domain of the client and a cost in dollar amount to the client. Upon receiving an interaction via a client device, details may be provided for each disruption. The details may include a severity and a number of items impacted by each disruption.

Figure 22:
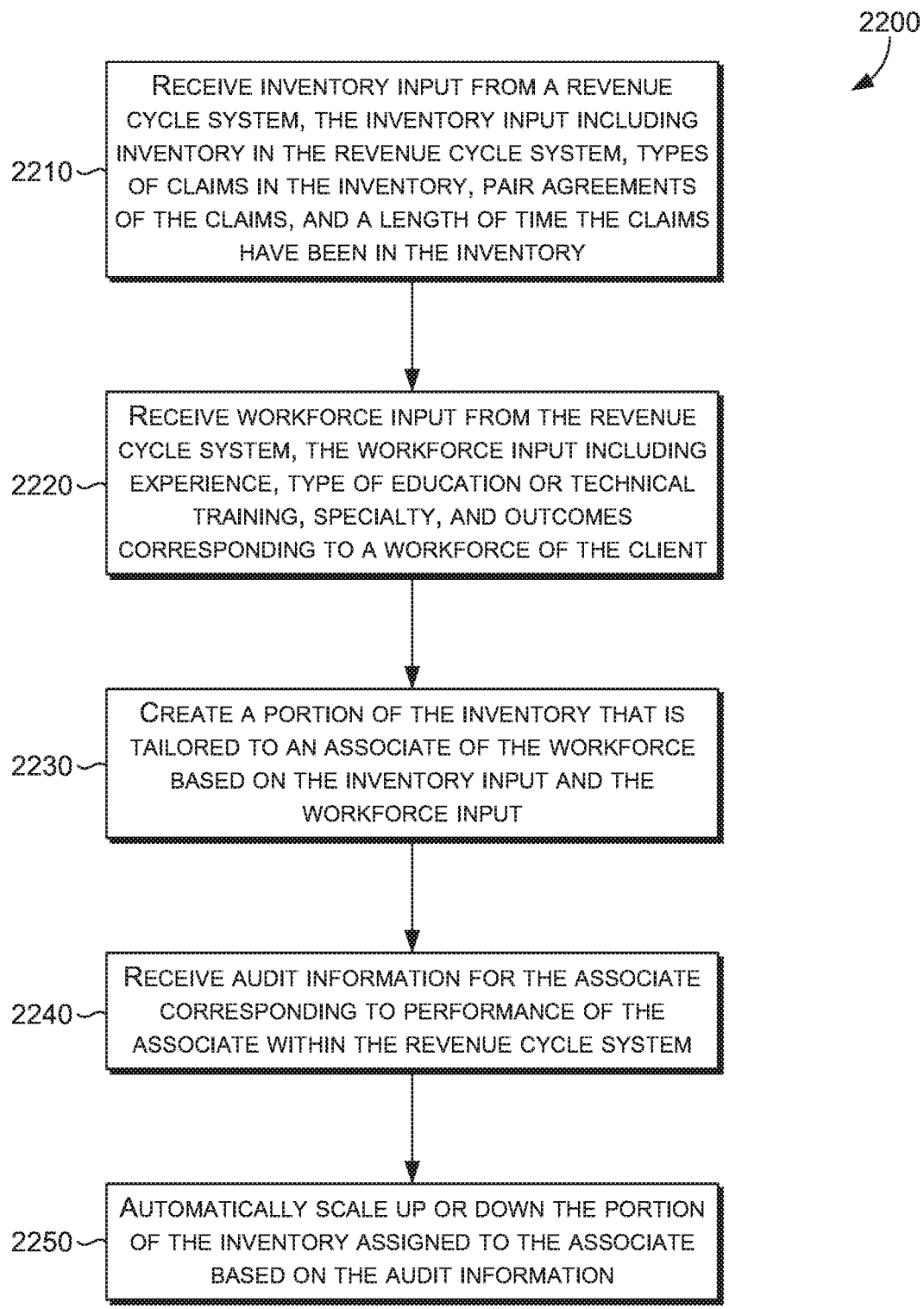
FIG. 22 is a flow diagram showing an exemplary method for optimizing workforce management in a revenue cycle management system, in accordance with various embodiments of the present invention.

Referring now to FIG. 22 a flow diagram is provided illustrating a method 2200 for providing revenue cycle workforce management, in accordance with an embodiment of the present invention. Method 2200 may be performed by any computing device (such as computing device described with respect to FIG. 1) with access to a revenue cycle management system (such as the one described with respect to FIG. 2) or by one or more components of the revenue cycle management system.

Initially, as shown at step 2210, inventory input is received from a revenue cycle system. The inventory input includes inventory in the revenue cycle system, types of claims in the inventory, pair agreements of the claims, and a length of time the claims have been in the inventory.

At step 2220, workforce input is received from the revenue cycle system. The workforce input includes experience, type of education or technical training, specialty, and outcomes corresponding to a workforce of the client.

At step 2230, a portion of the inventory is automatically assigned to an associate of the workforce. The portion of the inventory is tailored to the associate based on the inventory input and the workforce input.

In some embodiments, as shown at step 2240, audit information is received for the associate corresponding to performance of the associate within the revenue cycle system.

In some embodiments, as shown at step 2250, the portion of the inventory assigned to the associate is automatically scaled up or down based on the audit information.

In some embodiments, diagnostic data from the revenue cycle system is utilized to automatically identify disruptions for a plurality of clients. Utilizing the diagnostic data, the disruptions for a client of the plurality of clients may be ranked based on an impact to the revenue cycle system and a time required to execute a correction for each disruption.

In some embodiments, the inventory corresponds to the disruptions for the client. The disruptions may include the disruptions include suppressions, edit failures, and denials. A recommendation may be provided for the associate to execute a correction for each disruption. The correction may include one or more of process design, configuration, or change in workflow.

As can be understood, the present invention provides systems, methods, and user interfaces for providing revenue cycle workforce management and/or revenue cycle inventory management. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more non-transitory computer storage media having computer-executable instructions embodied thereon, that when executed, perform operations, the operations comprising:
   tracking revenue cycle inventory for a client from one or more data stores associated with the client, the revenue cycle inventory including data corresponding to patients from preregistration through final payment of a balance;
   analyzing, at a surveillance system, a particular data point within the revenue cycle inventory to
      automatically identify suppressions, edit failures, and denials as disruptions in a revenue cycle, and
      determine a count of claims affected by a disruption of the disruptions, a total outstanding balance due to the disruption, and a time required for an associate to execute a correction for the disruption;
   receiving, at a workforce management system, inventory input of the client, the inventory input including inventory in a revenue cycle management system, types of claims in the inventory, pair agreements of the claims, and a length of time the claims have been in the inventory;
   utilizing the inventory input to identify and recommend one of a process design, a configuration, or a change in workflow as a particular correction to execute for the disruption;
   receiving, at the workforce management system, workforce input, the workforce input including experience, type of education or technical training, specialty, and outcomes corresponding to a workforce to address the disruption of the client;
   automatically assigning, by the workforce management system, a particular associate of the workforce to execute the particular correction for the disruption;
   generating and displaying in an interactive user interface of a client device a dashboard that identifies the disruption;
   upon receiving an interaction by the dashboard on the client device, generating and displaying a screen display in the interactive user interface of the client device that provides details that correspond to the disruption to the particular associate in the interactive user interface, wherein the details include the display in the interactive user interface a user-selectable revenue cycle of the count of claims and the total outstanding balance for the disruption; and
   generating and displaying in the interactive user interface of the client device a recommendation for the particular associate to execute the particular correction for the disruption.

2. The media of claim 1, further comprising receiving audit information for the associate corresponding to performance of the associate within the revenue cycle management system.

3. The media of claim 2, further comprising automatically scaling up or down a portion of the inventory assigned to the associate based on the audit information.

4. The media of claim 1, further comprising, utilizing diagnostic data, automatically identify the disruptions in the revenue cycle management system across a plurality of clients.

5. The media of claim 4, further comprising, utilizing the diagnostic data, automatically rank the disruptions for the client of the plurality of clients based on an impact to the revenue cycle management system and a time required to execute a correction for each disruption.

6. The media of claim 5, wherein the inventory corresponds to the disruptions for the client.

7. The media of claim 6, further comprising providing a recommendation for the associate to execute the correction for each disruption of the disruptions.

8. A computerized method comprising:
   tracking revenue cycle inventory for a client from one or more data stores associated with the client, the revenue cycle inventory including data corresponding to patients from preregistration through final payment of a balance;
   analyzing, at a surveillance system, a particular data point within the revenue cycle inventory to
      automatically identify suppressions, edit failures, and denials as disruptions in a revenue cycle and
      determine a count of claims affected by a disruption of the disruptions, a total outstanding balance due to the disruption, and a time required for an associate to execute a correction for the disruption;
   receiving inventory input from a revenue cycle management system, the inventory input including inventory in a revenue cycle management system, types of claims in the inventory, pair agreements of the claims, and a length of time the claims have been in the inventory;
   utilizing the inventory input to identify and recommend one of a process design, a configuration, or a change in workflow as a particular correction to execute for the disruption;
   receiving workforce input from the revenue cycle management system, the workforce input including experience, type of education or technical training, specialty, and outcomes corresponding to a workforce to address the disruption of the client;
   automatically assigning, by the workforce management system, a particular associate of the workforce to execute the particular correction for the disruption;
   generating and displaying in an interactive user interface of a client device a dashboard that identifies the disruption;
   upon receiving an interaction by the dashboard on the client device, generating a screen display in the interactive user interface of the client device that provides details that correspond to the disruption to the particular associate in the interactive user interface, wherein the details include the display in the interactive user interface a user-selectable revenue cycle of the count of claims and the total outstanding balance for the disruption; and generating and displaying in the interactive user interface of the client device a recommendation for the particular associate to execute the particular correction for the disruption.

9. The method of claim 8, further comprising, utilizing diagnostic data from the revenue cycle management system, automatically identify the disruptions for a plurality of clients.

10. The method of claim 9, further comprising, utilizing the diagnostic data, automatically rank the disruptions for the client of the plurality of clients based on an impact to the revenue cycle management system and a time required to execute a correction for each disruption, wherein the impact is determined based on the count of claims affected by the disruption and the total outstanding balance due to the disruption.

11. The method of claim 10, wherein the inventory corresponds to the disruptions for the client.

12. The method of claim 10, further comprising providing a recommendation for the associate to execute the correction for each disruption.

13. The method of claim 8, further comprising:
receiving, at the workforce management system, audit information for the associate corresponding to performance of the particular associate within the revenue cycle management system; and
automatically scaling up or down the portion of the inventory assigned to the particular associate based on the audit information.

14. The method of claim 8, wherein the client device is an associate device that is configured to present information to the particular associate using a display.

15. The method of claim 8, further comprising:
identifying a plurality of disruptions in the revenue stream; and
automatically ranking the plurality of disruptions based at least in part on impact to the revenue system of each disruption in the plurality of disruptions.

16. A computerized system comprising:
one or more data stores that are associated with a client;
a client device that is associated with a particular associate;
one or more processors; and
a non-transitory computer storage media storing computer-useable instructions that, when used by the one or more processors, cause the one or more processors to:
track revenue cycle inventory for the client from the one or more data stores associated with the client, the revenue cycle inventory including data corresponding to patients from preregistration through final payment of a balance;
analyze, at a surveillance system, a particular data point within the revenue cycle inventory to
automatically identify suppressions, edit failures, and denials as disruptions in a revenue cycle and determine a count of claims affected by a disruption of the disruptions, a total outstanding balance due to the disruption, and a time required for an associate to execute a correction for the disruption;
receive inventory input from a revenue cycle management system of the client, the inventory input including inventory in a revenue cycle management system, types of claims in the inventory, pair agreements of the claims, and a length of time the claims have been in the inventory;
utilize the inventory input to identify and recommend one of a process design, a configuration, or a change in workflow as a particular correction to execute for the disruption;
receive, at a workforce management system, workforce input, the workforce input including experience, type of education or technical training, specialty, and outcomes corresponding to a workforce to address the disruption of the client;
automatically assign, by the workforce management system, a particular associate of the workforce to execute the particular correction for the disruption;
receive, at the workforce management system, audit information for the particular associate corresponding to performance of the particular associate within the revenue cycle management system;
in response to receiving the audit information, automatically scale up or down a portion of the inventory assigned to the particular associate based on the audit information;
generate and display in an interactive user interface of a client device a dashboard that identifies the disruption;
upon receiving an interaction by the dashboard on the client device, generate a screen display in the interactive user interface of the client device that provides information that corresponds to the disruption to the particular associate in the interactive user interface, wherein the information includes the display in the interactive user interface a user-selectable revenue cycle of the count of claims and the total outstanding balance for the disruption; and
generate and display in the interactive user interface of the client device a recommendation for the particular associate to execute the particular correction for the disruption.

17. The system of claim 16, further comprising, utilizing diagnostic data from the revenue cycle management system, automatically identify the disruptions for a plurality of clients.

18. The system of claim 17, further comprising, utilizing the diagnostic data, automatically rank the disruptions for a client of the plurality of clients based on an impact to the revenue cycle management system and a time required to execute a correction for each disruption of the disruptions.

19. The system of claim 18, further comprising providing a recommendation for the associate to execute the correction for each disruption.

* * * * *